US010595749B1

(12) United States Patent
Javitt et al.

(10) Patent No.: US 10,595,749 B1
(45) Date of Patent: Mar. 24, 2020

(54) INSOLE TO AID IN GAIT STABILITY

(71) Applicants: Naomi P Javitt, Hillside, NJ (US); Stephanie Yael Raphael, Plainview, NY (US)

(72) Inventors: Naomi P Javitt, Hillside, NJ (US); Stephanie Yael Raphael, Plainview, NY (US)

( * ) Notice: Subject to any disclaimer, the term of this patent is extended or adjusted under 35 U.S.C. 154(b) by 68 days.

(21) Appl. No.: 16/104,098

(22) Filed: Aug. 16, 2018

Related U.S. Application Data

(60) Provisional application No. 62/549,366, filed on Aug. 23, 2017.

(51) Int. Cl.
*A61B 5/103* (2006.01)
*A61F 5/14* (2006.01)
(Continued)

(52) U.S. Cl.
CPC .......... *A61B 5/1038* (2013.01); *A43B 3/0005* (2013.01); *A61B 5/486* (2013.01);
(Continued)

(58) Field of Classification Search
CPC ... A61B 5/6812; A61B 5/6807; A61B 5/6829; A61B 5/1038; A61B 5/112; A61B 5/486;
(Continued)

(56) References Cited

U.S. PATENT DOCUMENTS 6,807,869 B2 * 10/2004 Farringdon .......... A61B 5/1038
73/862.046
7,191,644 B2 * 3/2007 Haselhurst .......... A43B 3/0005
73/172

(Continued)

FOREIGN PATENT DOCUMENTS

WO WO-2013038214 A2 * 3/2013 .......... A61B 5/1038

OTHER PUBLICATIONS

Mckinney, Zach, et al. IEEE Haptics Symposium (HAPTICS) "Pilot Evaluation of Wearable Tactile Biofeedback System for Gait Rehabilitation in Peripheral Neuropathy" (2014).
(Continued)

*Primary Examiner* — John Villeccco
(74) *Attorney, Agent, or Firm* — Kane Kessler, P.C.; Barry E. Negrin

(57) ABSTRACT

A pair of electronic shoe insoles aids an individual with peripheral neuropathy in walking without falling, despite the user having little or no sensation in her feet. Each insole uses a number of pressure sensors and provides various forms of biofeedback to the user such as auditory, haptic, and vibratory feedback which corresponds to the position of the user's foot on the ground. Vibration feedback is provided through vibration motors disposed against the soles of the user's feet at selected locations which correspond to locations of pressure sensors. This allows for direct neural stimulation of the sole of the foot at three biomechanically appropriate locations. Auditory and haptic feedback are provided through auxiliary devices that the user wears on appropriate parts of the body. Biofeedback transmitted through these mechanisms would correspond to change in foot position as detected by the pressure sensors. The shoe insoles may provide one or more of these forms of feedback, and other types of feedback may be provided by output devices as well. An embedded microcontroller wirelessly connected to a computer, tablet or phone permits an individual to monitor gait performance and to adjust numerous parameters of this biofeedback mechanism, such as time delays and strength of vibration or audio feedback. The device may also include a driving mode in which small variations of pressure on the gas pedal would be conveyed to the user through haptic and auditory feedback, thereby allowing the user to drive.

21 Claims, 6 Drawing Sheets

(51) Int. Cl.
  *A63B 5/00* (2006.01)
  *A43B 3/00* (2006.01)
  *A61B 5/00* (2006.01)

(52) U.S. Cl.
  CPC ............ *A61B 5/6812* (2013.01); *A61B 5/742* (2013.01); *A61B 5/7415* (2013.01); *A61B 5/7455* (2013.01); *A61F 5/14* (2013.01); *A61B 2562/0247* (2013.01)

(58) Field of Classification Search
  CPC ................ A61B 5/7455; A61B 5/7415; A61B 2562/00247; A61F 5/0111; A61F 5/0127; A61F 5/14; A43B 3/0005; A43B 17/00; A63B 24/0062
  See application file for complete search history.

(56) References Cited

U.S. PATENT DOCUMENTS

| | | | |
|---|---|---|---|
| 7,997,007 B2 | 8/2011 | Sanabria-Hernandez | |
| 8,011,229 B2* | 9/2011 | Lieberman | A61B 5/1036 73/65.01 |
| 8,844,166 B2* | 9/2014 | Jazdanian | A43B 3/0005 36/43 |
| 8,968,218 B2* | 3/2015 | Wukasch | A61B 5/1038 600/587 |
| 8,974,402 B2* | 3/2015 | Oddsson | A61B 5/6829 600/595 |
| 9,279,734 B2* | 3/2016 | Walker | G01L 1/2206 |
| 9,375,570 B2* | 6/2016 | Kiani | A61B 5/6898 |
| 9,389,057 B2* | 7/2016 | Meschter | H04N 5/9205 |
| 9,510,776 B2* | 12/2016 | Lee | A61B 5/6829 |
| 9,549,585 B2* | 1/2017 | Amos | G01L 1/22 |
| 9,565,286 B2* | 2/2017 | Chung | H04W 76/14 |
| 9,993,181 B2* | 6/2018 | Ross | A61B 5/112 |
| 10,004,428 B2* | 6/2018 | Everett | A61B 5/1036 |
| 10,070,680 B2* | 9/2018 | Molyneux | A63B 60/46 |
| 10,159,427 B2* | 12/2018 | Malawey | A61B 5/1038 |
| 10,213,134 B2* | 2/2019 | Markison | A61B 5/02055 |
| 10,238,316 B2* | 3/2019 | Malawey | A61B 5/1038 |
| 10,327,700 B2* | 6/2019 | Lee | A61B 5/6807 |
| 10,363,453 B2* | 7/2019 | Fitzgerald | G01C 22/006 |
| 10,398,189 B2* | 9/2019 | Amos | A61B 5/6807 |
| 10,470,711 B2* | 11/2019 | Yuan | A61B 5/6829 |
| 2003/0097878 A1* | 5/2003 | Farringdon | A61B 5/1038 73/819 |
| 2007/0173903 A1* | 7/2007 | Goren | A61N 1/32 607/49 |
| 2007/0203435 A1 | 8/2007 | Novack | |
| 2007/0203533 A1* | 8/2007 | Goren | A61N 1/32 607/49 |
| 2008/0282580 A1* | 11/2008 | Ji-Woog | A61F 5/14 36/140 |
| 2008/0287832 A1* | 11/2008 | Collins | A43B 3/0005 600/587 |
| 2008/0306410 A1* | 12/2008 | Kalpaxis | A61B 5/0002 600/592 |
| 2009/0240171 A1* | 9/2009 | Morris Bamberg | A61B 5/1038 600/595 |
| 2009/0284368 A1* | 11/2009 | Case, Jr. | A43B 3/0005 340/539.1 |
| 2009/0293319 A1* | 12/2009 | Avni | G01L 5/008 36/132 |
| 2010/0152619 A1* | 6/2010 | Kalpaxis | A61B 5/0002 600/592 |
| 2010/0324455 A1* | 12/2010 | Rangel | A43B 7/147 600/592 |
| 2011/0054359 A1* | 3/2011 | Sazonov | A43B 3/0005 600/595 |
| 2012/0109013 A1* | 5/2012 | Everett | A61B 5/1036 600/587 |
| 2012/0291563 A1* | 11/2012 | Schrock | A43B 3/00 73/862.041 |
| 2012/0291564 A1* | 11/2012 | Amos | A61B 5/6807 73/862.045 |
| 2013/0006152 A1* | 1/2013 | Lee | A61B 5/1038 600/595 |
| 2013/0211290 A1* | 8/2013 | Lee | A43B 3/0005 600/592 |
| 2013/0236867 A1* | 9/2013 | Avni | G09B 19/00 434/247 |
| 2014/0266570 A1* | 9/2014 | Sharma | G09B 21/003 340/4.12 |
| 2015/0100104 A1* | 4/2015 | Kiani | A61N 1/36003 607/49 |
| 2015/0100107 A1* | 4/2015 | Kiani | A61B 5/0488 607/59 |
| 2015/0133825 A1* | 5/2015 | Wukasch | A61B 5/1038 600/595 |
| 2016/0058326 A1* | 3/2016 | Winfree | A61B 5/112 600/592 |
| 2016/0324445 A1* | 11/2016 | Kim | A61B 5/112 |
| 2016/0367191 A1* | 12/2016 | Esposito | A61B 5/1038 |
| 2017/0026504 A1* | 1/2017 | Nichols | H04M 1/7253 |
| 2017/0116869 A1 | 4/2017 | Pape | |
| 2017/0128816 A1 | 5/2017 | DeMarch | |
| 2017/0135607 A1* | 5/2017 | Morris Bamberg | A61B 5/1038 |
| 2017/0164899 A1* | 6/2017 | Yang | A61B 5/6807 |
| 2017/0188950 A1* | 7/2017 | Gazdag | A61B 5/6807 |
| 2018/0028862 A1* | 2/2018 | Statham | A61B 5/6895 |
| 2018/0092572 A1* | 4/2018 | Sanchez | G06K 9/00342 |
| 2018/0158542 A1* | 6/2018 | Kim | G16H 15/00 |
| 2018/0263532 A1* | 9/2018 | Smulyan | A61B 5/112 |
| 2018/0279915 A1* | 10/2018 | Huang | A61B 5/002 |
| 2018/0333078 A1* | 11/2018 | Malawey | A61B 5/1038 |
| 2018/0333080 A1* | 11/2018 | Malawey | A61B 5/1038 |
| 2018/0336798 A1* | 11/2018 | Malawey | G09B 19/0038 |
| 2019/0000177 A1* | 1/2019 | Dervish | A43B 3/0005 |
| 2019/0000352 A1* | 1/2019 | Everett | A61B 5/1036 |
| 2019/0066532 A1* | 2/2019 | Bennett | G09B 19/003 |
| 2019/0105217 A1* | 4/2019 | Prattichizzo | A61B 5/1038 |
| 2019/0175106 A1* | 6/2019 | Langer | A61B 5/6807 |
| 2019/0254568 A1* | 8/2019 | Nino | A43B 3/0005 |
| 2019/0290167 A1* | 9/2019 | Everett | A61B 5/6807 |
| 2019/0374153 A1* | 12/2019 | Oddsson | A61B 5/4561 |

OTHER PUBLICATIONS

Menz, Hylton B., et al., study published in the Archives of Physical Medicine and Rehabilitation, 2004; 85:245-52 entitled "Walking Stability and Sensorimotor Function in Older People with Diabetic Peripheral Neuropathy".

Ducic MD, Ivica et al., study published in the Annals of Plastic Surgery, vol. 52, No. 6, Jun. 2004, entitled "Relationship Between Loss of Pedal Sensibility, Balance, and Falls in Patients with Peripheral Neuropathy".

Stambolieva, Katerina et al., (2017) Positive effects of plantar vibration training for the treatment of diabetic peripheral neuropathy: A pilot study, Somatosensory & Motor Research, 34:2, 129-133.

* cited by examiner

INSOLE TO AID IN GAIT STABILITY

CROSS REFERENCE TO RELATED APPLICATIONS

This application claims the benefit of provisional patent application Ser. No 62/549,366, filed 2017 Aug. 23 by the present inventors.

BACKGROUND—PRIOR ART

The following is a tabulation of some prior art that presently appears relevant:

| U.S. patents | | | |
| --- | --- | --- | --- |
| Patent No. | Kind Code | Issue Date | Patentee |
| 7,997,007 | B2 | Aug. 16, 2011 | Sanabria-Hernandez |

| U.S. patent Application Publications | | | |
| --- | --- | --- | --- |
| Publication Nr. | Kind Code | Publ. Date | Applicant |
| 2007/0203435 | A1 | Aug. 30, 2007 | Novack |
| 2017/0128816 | A1 | May 05, 2017 | DeMarch |
| 2017/0116869 | A1 | Apr. 24, 2017 | Pape |

NONPATENT LITERATURE DOCUMENTS

Mckinney, Zach, et al. *IEEE Haptics Symposium (HAPTIC-S)* "Pilot Evaluation of Wearable Tactile Biofeedback System for Gait Rehabilitation in Peripheral Neuropathy." (2014)

FIELD OF THE INVENTION

The invention relates to devices intended to improve gait through the use of biofeedback. In particular, this invention is intended for use by people with peripheral neuropathy to alert the user to the position of their foot on the ground as they walk. The device uses pressure sensors on an insole to detect foot position, and provides feedback to the user through vibration, auditory, and pressure feedback. This sensory substitution device will improve the balance and gait of those with peripheral neuropathy or other neurological disorders that cause damage to nerves in the feet.

DESCRIPTION OF THE RELATED ART

Over 20 million people in the United States suffer from peripheral neuropathy, which is a condition that causes damage to the nervous system. Peripheral neuropathy is common among the elderly and is often a result of diabetes. As lifespan increases and diabetes becomes more prevalent, peripheral neuropathy is expected to become more common as well. The nerve damage caused by peripheral neuropathy often causes weakened sensitivity to a variety of sensations, including pain, heat, and position. The location of this nerve damage often correlates to the distance of the part of the body from the central nervous system. This means that the feet and toes are often the first parts of the body to be affected by peripheral neuropathy. An inability to sense motion and position in the feet as a result of peripheral neuropathy causes instability, making those with peripheral neuropathy highly susceptible to falls. This is because the nerves on the bottom of their feet are not fully functional, so affected individuals do not know how their feet are positioned as they walk. These falls often result in hospitalization due to broken bones. Once in the hospital, these people are likely to catch diseases such as pneumonia, which could lead to death. This sequence of events after falling is exceedingly common among the elderly, and because instability due to peripheral neuropathy is also common among the elderly, restoring balance to those with peripheral neuropathy can prevent this chain of events from occurring in the first place. Because fatal falls are so common among this population, many of these individuals become homebound because they do not want to risk their safety by walking outside of their homes.

A study published in the Archives of Physical Medicine and Rehabilitation, Volume 85, entitled "Walking Stability and Sensorimotor Function in Older People with Diabetic Peripheral Neuropathy" addressed the role of diabetic peripheral neuropathy in gait pattern and stability. It was found that "Older people with DPN (diabetic peripheral neuropathy) have an impaired ability to stabilize their body", giving "further insights into the role of peripheral sensory input in the control of gait stability". In addition, a study was published in Annals of Plastic surgery Volume 52, June 2004, focusing on the relationship between balance and sensitivity in patients with impaired sensation in the lower part of the body. This study showed that "in patients with peripheral neuropathy, gait and balance disturbances are a result of systematic dysfunction of peripheral nerves".

There is little that can be done to restore function to nerves that have been damaged. Because of this, those with peripheral neuropathy must adapt to their weakened sensitivity. It is common for those with peripheral neuropathy to constantly look at their feet while walking, as this is the only way to be sure of their foot position. However this means that those with peripheral neuropathy must walk very slowly and are constantly be focused on their foot position to maintain stability. They often adjust their gait by taking much smaller steps as well. Currently there are no walking aids on the market directed towards the nerve damage of those with peripheral neuropathy. Many people with peripheral neuropathy use canes or walkers, however these do not directly address their needs, as they compensate for damaged muscles and for imbalance, but not damaged nerves. Canes and walkers may often be ineffective as well because peripheral neuropathy often damages the hands as well as the feet. Because of this, it is difficult for those with peripheral neuropathy to hold on to a cane or walker. There is a need for a device that is suited towards the needs and abilities of those with peripheral neuropathy. Many of these individuals have functioning leg muscles but are unable to use them effectively because of their inability to detect how their feet are positioned.

A device is needed to provide sensory compensation for damaged nerves in the feet. The use of sensory substitution would be the most suitable walking aid for those with peripheral neuropathy because it would directly address their lack of sensitivity, thereby solving the problem at the source to make them more stable. Sensory substitution compensates for a lack of sensitivity in one area by providing sensory feedback through an alternative sense that is fully functional. In those with peripheral neuropathy, their loss of sense of position and motion may be replaced by alternative forms of feedback, such as auditory feedback or sensation on other parts of the body that have not been damaged by peripheral neuropathy.

Vibration is often suggested as a method for enhancing sensitivity in the feet of those with peripheral neuropathy as vibration, motion, and position are all sensed by the large nerve fibers. Stimulating these same nerve fibers through vibration may increase sensitivity to motion and position. A study entitled "Positive effects of plantar vibration training for the treatment of peripheral neuropathy: A pilot study", published in Somatosensory and Motor Research, Volume 34 showed that "mechanical stimulation of foot mechanoreceptors can be useful to alter the proprioceptive feedback and in this way to improve postural stability." It is also shown in this study that " . . . the vibratory noise enhancement of the foot sole sensory information might improve signal detection and transmission from tactile sensors." U.S. Patent Application No. 2007/0203435 provides a device to aid with balance and gait by stimulating the nerves through vibration. The vibrations from this device are activated by pressure sensors as the wearer puts weight on each foot giving the user a heightened sense of position as they walk. While this takes advantage of vibration and its role in balance, it is not sufficient for many people with peripheral neuropathy. The heightened sensitivity caused by vibration is very subtle, particularly for those people with more severe peripheral neuropathy that may have lost the majority of sensation in their feet. This form of stimulation may not be felt by many people with peripheral neuropathy, meaning that it will not be able to improve their balance. As a result, people with more severe peripheral neuropathy would still not be able to walk with the aid of this device because the nerves on the bottom of their feet are so significantly damaged that vibration would not be sufficient. A device that provides alternative forms of feedback to parts of the body that have not been affected by peripheral neuropathy would be more effective in improving stability by allowing for sensory substitution. The inability of this device to provide multiple forms of alternative feedback makes it ineffective in providing safety for many with peripheral neuropathy.

Mats are often used to aid in the gait training of those with neurological disorders. U.S. Patent Application No. 2017/0128816 to DeMarch teaches a mat that senses pressure as the user walks on it, and provides auditory and visual feedback as the user activates targets with their feet. This device, while useful in training patients to walk properly, is completely stationary and therefore cannot be used throughout regular daily activity and is simply a training device. People with peripheral neuropathy have ongoing nerve damage, and no amount of training will be able to correct for a loss of sensation. There is still a need for a wearable device to provide multisensory biofeedback to those with peripheral neuropathy, which would allow them to improve their balance and prevent falling through sensory substitution.

A device that contains pressure sensors to be worn on the bottom of the feet and provide sensory feedback is disclosed in U.S. Pat. No. 7,997,007 to Sanabria Hernandez (2011). This device is used to correct issues such as "toe-walking" or "heel-walking" by sensing the position of the user's feet and providing feedback through, auditory, visual, and physical stimulation. This invention however, does not optimize the locations of pressure sensors to accurately detect all phases of gait. It also may correct problems in walking but does not have alternative functions to aid users as they drive, and does not specify which forms of physical stimulation should be used, meaning it does not teach on what forms of stimulation should be used and how to use them, other than auditory stimulation. The auditory feedback is also provided by a speaker located in the shoe, meaning that this device would be disruptive to those around the person wearing the invention. Because of this it is unlikely that a person would be able to use a device such as this outside of the home and in the presence of other people. This invention also does not provide for vibration as a form of stimulation, and for those with peripheral neuropathy, vibratory stimulation on the bottom of the foot would be particularly effective in amplifying the sensation of walking. The device also requires the use of visual stimulation, which would not be suitable for use throughout daily activity as it would require the constant attention of the user.

A need for a multisensory biofeedback system that is suitable for the needs of those with peripheral neuropathy is not provided for in any of the art. A device is needed that will ensure safety and mobility of those with peripheral neuropathy by providing a range of feedback that can be fit to the needs of the user and allow for sensory substitution. While a single biofeedback system such as vibration may help some with moderate nerve damage, it is necessary to create a multisensory biofeedback system to fit the varying needs and capabilities of those with peripheral neuropathy. In Mckinney, Zach, et al. a "Pilot Evaluation of Wearable Tactile Biofeedback System for Gait Rehabilitation in Peripheral Neuropathy" was published in 2014 IEEE Haptics Symposium. It was said that " . . . it is clear that both biofeedback devices and proactive physical therapy programs have much potential for PN rehabilitation . . . " and "Substantial changes in clinically meaningful gait parameters such as walking velocity and stride length with feedback active corroborate the potential of biofeedback as a rehabilitation tool . . . " This proves the added benefit of creating a multisensory biofeedback system to aid those who suffer from peripheral neuropathy.

Driving is also an issue for those with peripheral neuropathy as they cannot feel the weight of their foot on the gas pedal, and especially are not aware of small changes in pressure that would cause the car to accelerate. As a result, many with peripheral neuropathy cannot drive, which restricts their freedom and mobility. Sensory substitution may also allow those with peripheral neuropathy to drive safely by detecting the weight of the foot on the gas pedal and providing this information to the driver through alternative biofeedback mechanisms such as auditory or visual feedback. There is no device currently that takes this approach to driving aids, as most driving aids use hand controls for those who cannot use their feet to drive.

Currently there is no mechanism suitable for both walking and driving for people with peripheral neuropathy, and there are no devices that take into account the needs of people with this disorder, as they often have weakened senses in their hands, damaged nerves in their feet, and loss of hearing. There is a need for a wearable system that can be easily adjusted to the capabilities of the user by providing a wide range of feedback mechanism to aid in improving balance and gait through the use of sensory substitution.

SUMMARY OF THE INVENTION

The invention provides a method for giving multisensory biofeedback to the user based on the position of their feet, thereby improving gait and balance in those with peripheral neuropathy. The invention also provides a system for medical professionals to monitor the gait of their patients by recording this information, as well as to adjust settings of the biofeedback system. Another function of the invention is to aid in driving by providing the user with biofeedback based on the pressure of the foot on the gas pedal, enabling them to drive safely. This invention uses sensory substitution to improve the safety and stability of those with peripheral neuropathy while walking by replacing their failing nerves in the feet with alternative feedback systems.

The invention accomplishes all of this by sensing when pressure is placed on various parts of the foot through sensors, and conveying that information to the user through biofeedback. Pressure sensors placed in the three main weight-bearing parts of the foot allow the device to sense when the user places weight on each part of the foot. Through multiple biofeedback systems, the user becomes aware of the position of their foot, leading to an increased stability and allowing them to prevent falls.

In a preferred embodiment, all electronic components will be contained in a set of orthotics inserts to be worn inside the shoe. These orthotic inserts should be waterproof to protect all components from damage. In a preferred embodiment, the orthotic inserts will be custom made to fit the contour of the user's foot and have room with in the inserts for the various electronics components. Batteries will be contained in these insoles and could be charged inductively through a mat. The battery life of the invention will be several hours, allowing the device to be charged at night while it is not being worn by the user. The invention will use a wireless communication system such as Bluetooth, Wi-Fi, or RF to communicate with biofeedback systems as well as a digital user interface that may be used by a medical professional to make adjustments to the device and to monitor the gait of the user.

As the wearer of these insoles takes a step, the pressure sensors detect the change in pressure as the user puts weight on various parts of their foot and the biofeedback mechanisms are activated accordingly. In a preferred embodiment, there are three forms of biofeedback to provide stimulus to the user. These forms of stimulation ideally include vibration on the bottom of the foot, auditory stimulation, and stimulation through a pressure cuff. Vibration will be provided by vibrating motors to be worn on the bottom of the foot. Auditory stimulation will be provided by a device to be worn on the ear of the user. The pressure cuff may be worn on any part of the body that is not damaged by peripheral neuropathy, preferably the upper arm or upper leg.

The vibrating motors will be placed inside the insole in locations corresponding to those of the three pressure sensors on each insole. Vibrations will be used as a feedback source in the invention to stimulate the large nerve fibers in the foot which sense vibration, motion, and position. The use of vibration will amplify the existing sensation of walking and require the least amount of training for the user.

Auditory stimulation will be provided by an earpiece, which in a preferred embodiment would be included in a hearing aid or provided by a Bluetooth headset. As the user puts pressure on various parts of their foot, it is detected by the sensors, this information will be transmitted to the auditory feedback device through a control center. Then the auditory feedback device will produce various audio tones, with a different tone corresponding to each sensor on the insole. The audio tones may also be transmitted through the user interface such as a phone or computer application. In a preferred embodiment each part of the foot will be associated with a different note on a standard scale. This allows the device to take advantage of the user's natural ability to recognize patterns in audio tones by associating each part of the foot with a music note. The user's brain, after some training, will know which part of the foot to put down even if the nerves are not fully function because they will recognize the pattern of the audio tones.

In the preferred embodiment feedback in the form of pressure will be provided by a pressure cuff to be worn on the upper arm or leg of the user, or any part of a limb that has not been significantly damaged by peripheral neuropathy as to render the pressure cuff ineffective. In a preferred embodiment the pressure cuff is to provide different amounts of pressure which would correspond to the locations of sensors on the foot.

Additional forms of feedback may include electrical stimulation, or visual feedback. The forms of biofeedback will be controlled by a microcontroller contained within the insoles, and the pressure cuff and earpiece will be activated by the microcontroller through Bluetooth or WiFi in one embodiment.

In a preferred embodiment, the invention will have separate settings to be enabled by the user while driving. In this driving mode, the feedback will be more sensitive to slight changes in pressure as the user changes how much weight they put on the gas pedal. Changes in pressure on the pedal will correspond to change in the biofeedback mechanisms. In a preferred embodiment, an increase in pressure will cause an increase in magnitude of vibration on the bottom of the foot and pressure on the arm, as well as an increased pitch of the audio tone in the earpiece. The stimulation through biofeedback will correspond to changes in pressure on the bottom of the foot, thereby communicating to the user how much pressure they have put on the gas pedal.

In a preferred embodiment, there is also a digital user interface to be used by a doctor or other trained professional to allow for the customization of the settings to each individual user. In this embodiment, some customizable parameters may include response time of feedback, volume and pitch of audio tones, strength of vibrations, and sensitivity of the pressure sensors. The interface would also have a graphical application to track the gait of the user and would allow the doctor to further analyze the gait of the user by storing data on the gait of the user. Some of the data to be recorded may include the amount of time between each step, and how much pressure is being placed on the different parts of the foot. This would provide useful information to the doctor because regularity of gait significantly increases stability, so measuring the change in time between each step of the user would indicate the progress of the patient to the doctor. The device would be able to store and transmit the data to the doctor through the communication module.

It is expected that it would take some training time for the user to adjust to the invention, as they would not immediately be used to the alternative forms of biofeedback. It is expected that it would take a few weeks for the user to adjust and for the sensory substitution to reach its full functionality. During this adjustment period, the user would be able to wear the device throughout daily activity and continue their regular walking habits. Through this process it is expected that the sensory substitution would slowly increase in efficacy as the user adapts to it.

DRAWINGS—FIGURES

DRAWINGS—REFERENCE NUMERALS

Figure 1:
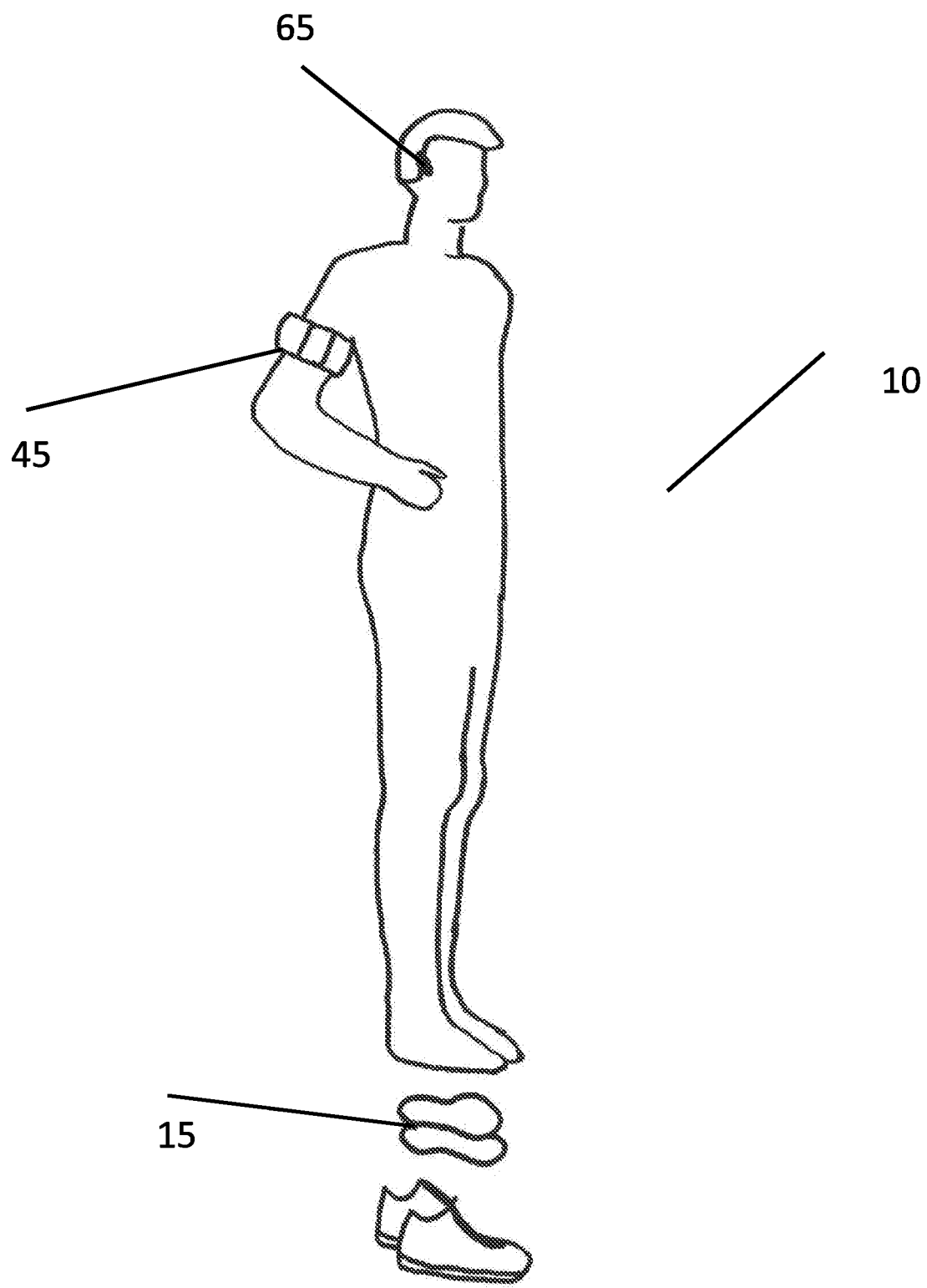
FIG. 1 shows one embodiment of the invention worn by the user.

10 Entire system
15 Orthotic Inserts
20 Pressure Sensors
25 Control Center
30 Vibrating motors
35 Microcontroller
40 Communication Module
45 Pressure Cuff
50 Auxiliary control center
55 Pressure Cuff band
65 Auditory device
70 Biofeedback devices
80 Digital user interface

DETAILED DESCRIPTION—FIGS. 1-7—PREFERRED EMBODIMENT

FIG. 1 Shows the insoles 15 which will contain embedded electronic components and will be inserted into a pair of shoes to be worn by the user. The auditory device 65 should be worn on the ear and the pressure cuff 45 may be worn above the knee or on any convenient part of the body. The invention will exist independently of the shoe, allowing the orthotic inserts to be easily inserted into a pair of shoes and to be transferred between different shoes by the user.

Figure 2:
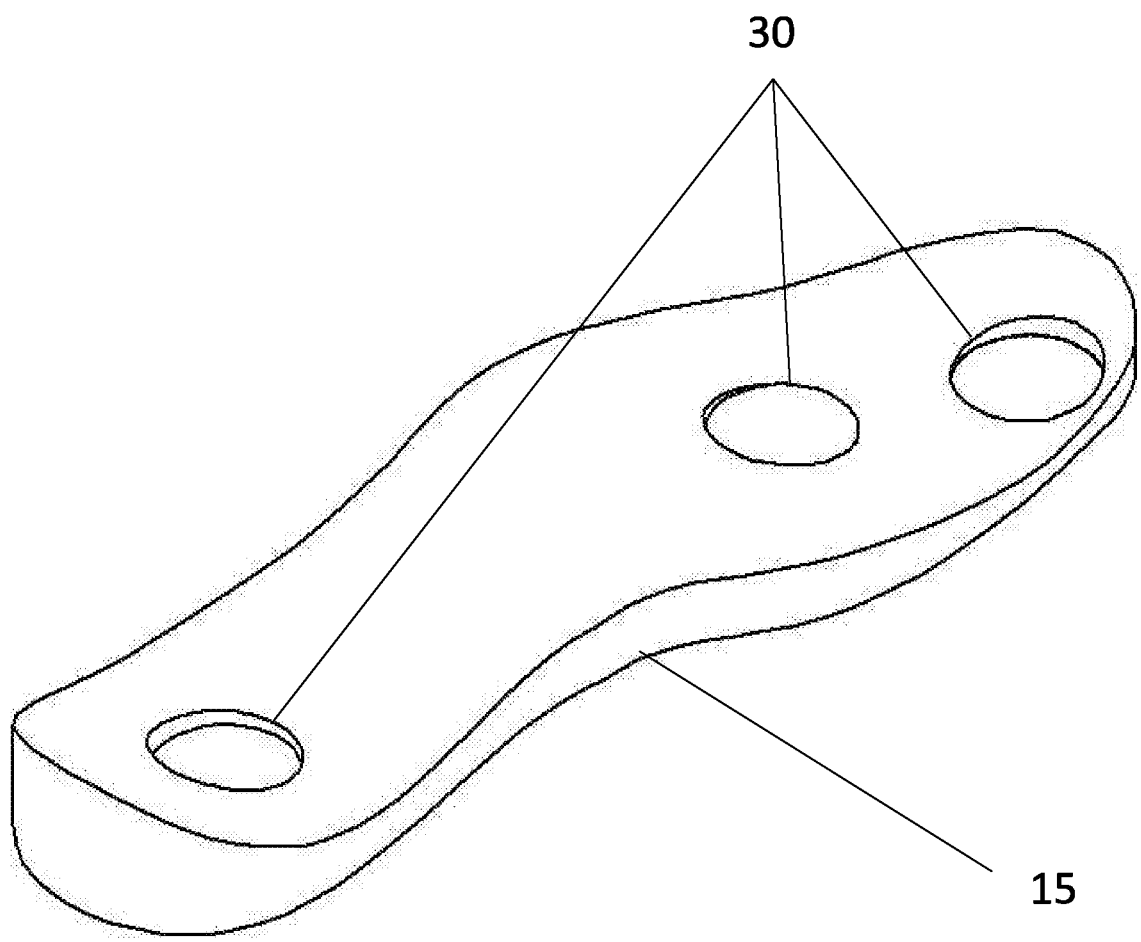
FIG. 2 is a perspective image of the insoles in an embodiment of the invention, with motors exposed to show placement.
Figure 3:
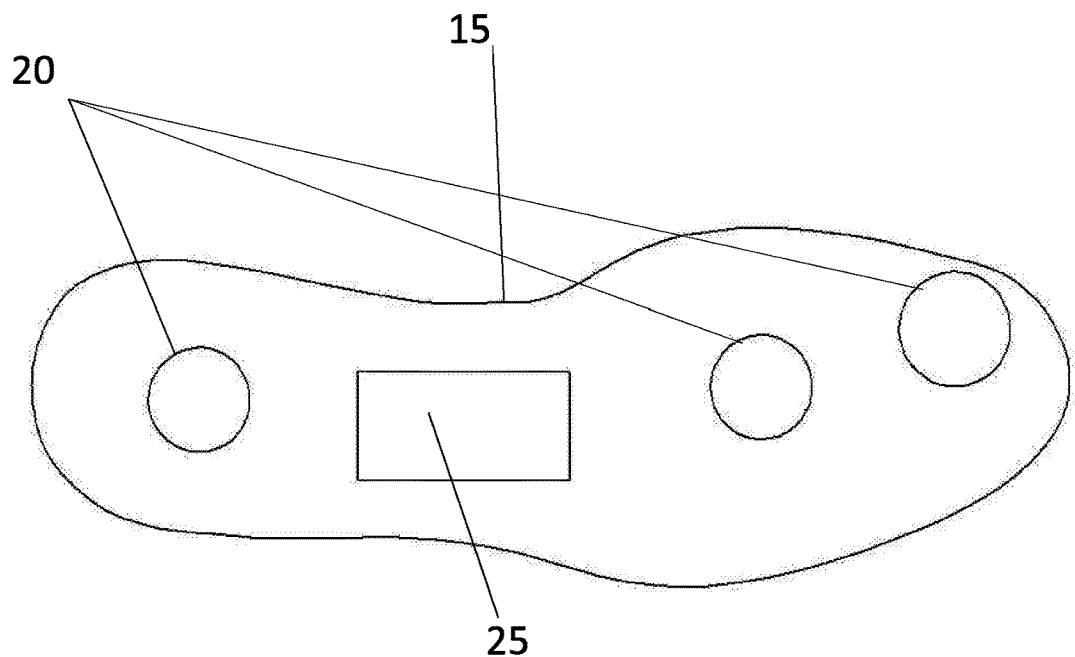
FIG. 3 is a bottom view of the invention, showing the pressure sensing components and unit containing a microcontroller and battery.
Figure 4:
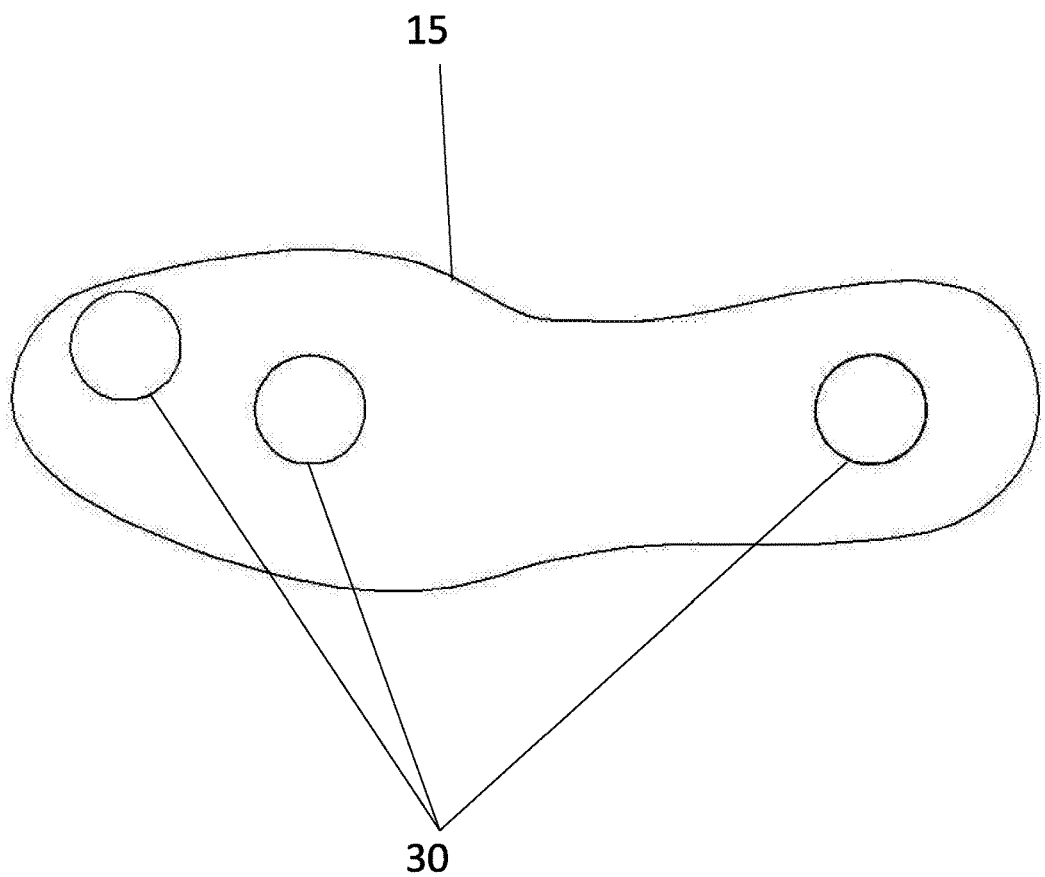
FIG. 4 is a top view of the insole with vibrating motors visible.

FIGS. 2-4 show an embodiment of the orthotic inserts 15, containing many electronic components including pressure sensors 20 connected to a control center 25, as well as several vibrating motors 30 connected to the control center. In a preferred embodiment, Interlink Electronics, Force Sensing Resistors™ 402 are used as pressure sensors 20, as is shown in the drawings. Alternatively, strain gauges may be used instead of force sensitive resistors to detect pressure of the user's foot on the ground throughout the gait cycle.

FIGS. 3 and 4 show the orthotic insert 15 which has a top face and bottom face. Each pressure sensor 20, located on the bottom face of the inserts, will have a vibrating motor 30 placed in the corresponding location on the top face of the insole. In a preferred embodiment, Jinlong coin vibration motors are used as vibrating motors 30. The pressure sensors will be located beneath the toe, ball of the foot, and heel. These three locations bear most of the user's weight, and the position of the user's weight shifts between these three locations throughout the gait cycle. By putting sensors in these three locations and conveying that information to the user through multisensory biofeedback, the user of the invention will be aware of how their foot is positioned on the ground, allowing them to walk with increased stability and reducing the risk of falling.

Figure 5:
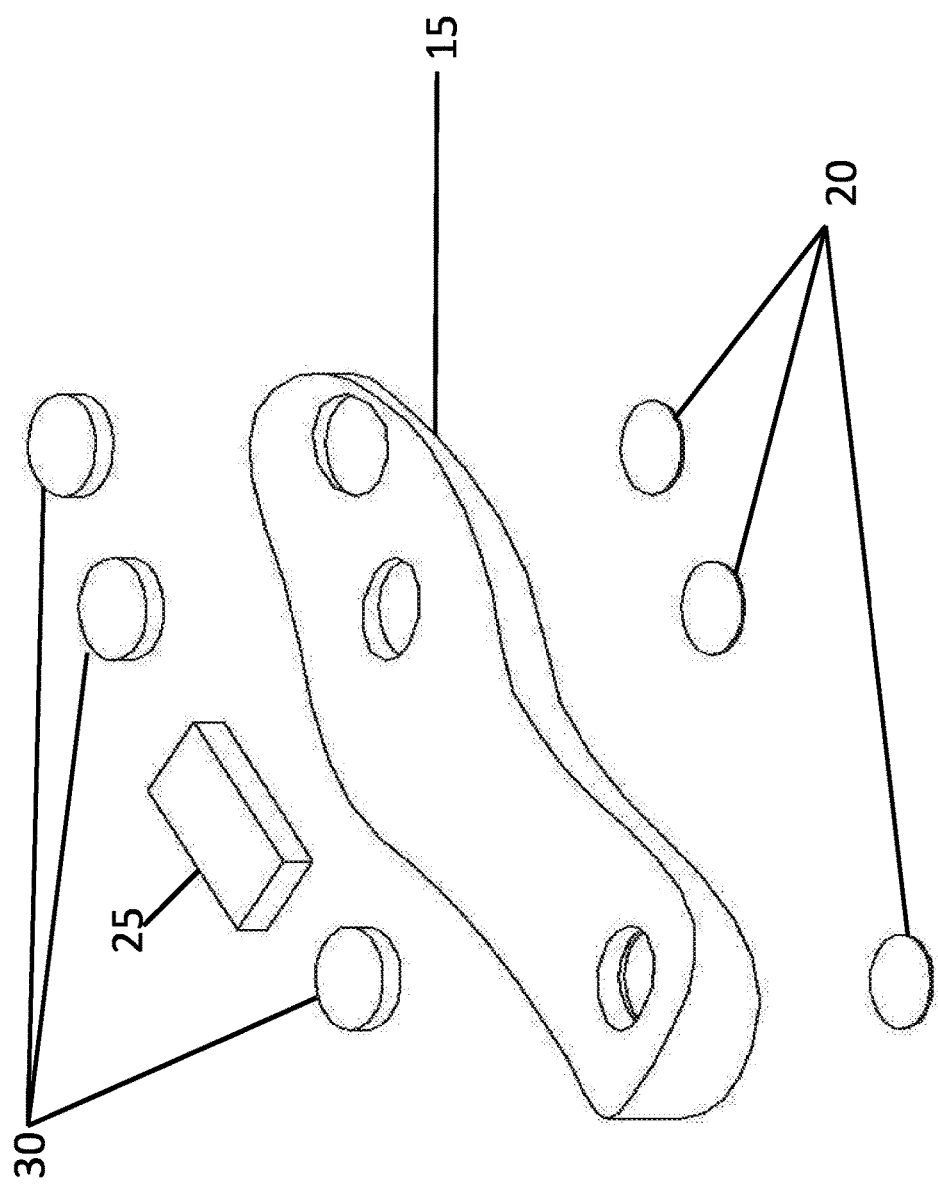
FIG. 5 is an exploded perspective of the insole with electronic components visible.

FIG. 5 shows through an exploded view the placement of sensors 20, vibrating motors and the microcontroller 25 within the orthotic insert 15.

Figure 6:
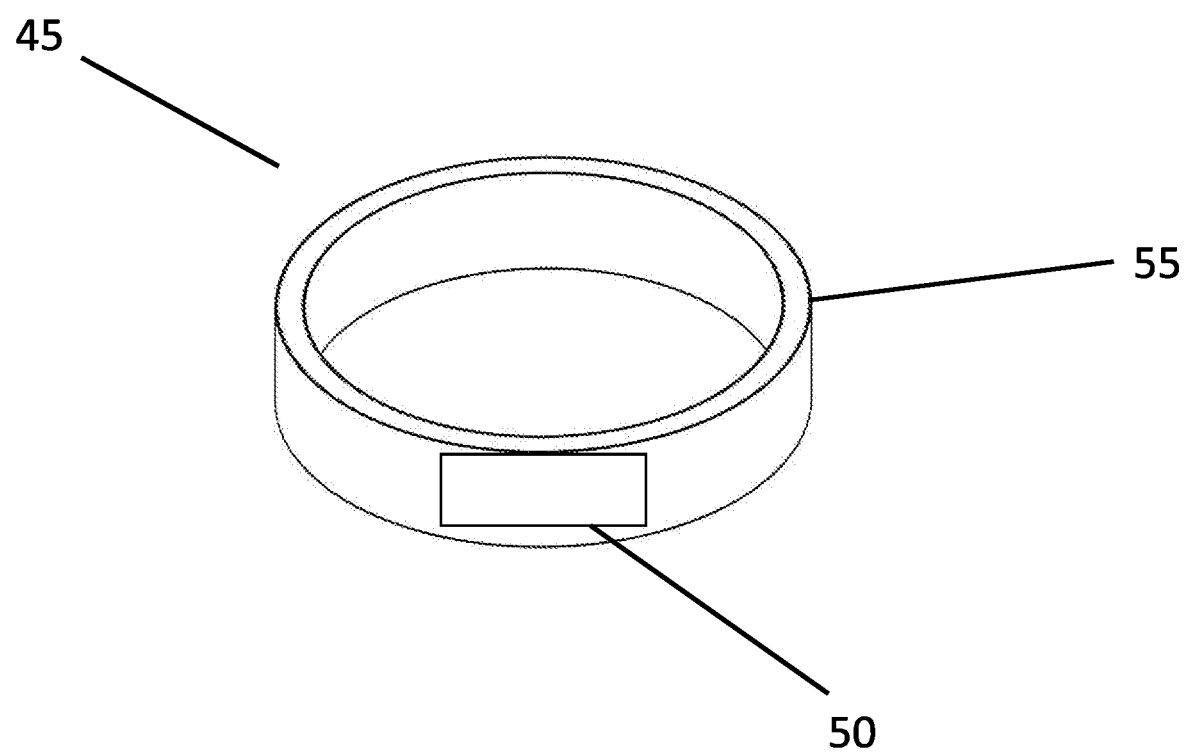
FIG. 6 is a pressure cuff to be worn on the upper arm in a possible embodiment of the invention.

FIG. 6 shows the pressure cuff 45 output device. The communication module 40 located in the control center 25 will be used to control the pressure cuff 45 through a receiver located in an auxiliary control center 50, which is located on the band 55 of the pressure cuff. The pressure cuff 45 will apply different amounts of pressure corresponding to the parts of the foot that are bearing the weight of the user. The communication module 40 will also control the auditory device 65, which in a preferred embodiment may be an existing Bluetooth headset that can be paired with the invention or may be designed separately in conjunction with this invention. Additionally, the invention may be paired with a hearing aid that has Bluetooth capabilities. Auditory device 65 will play different tones corresponding to the sensors on each part of the foot. As the user applies pressure to each of the sensors 20 the auditory device 65 will play the corresponding tone as one of the forms of the biofeedback 70. In a preferred embodiment, auditory device 65 is paired with communication module 40, which is controlled by microcontroller 35.

Figure 7:
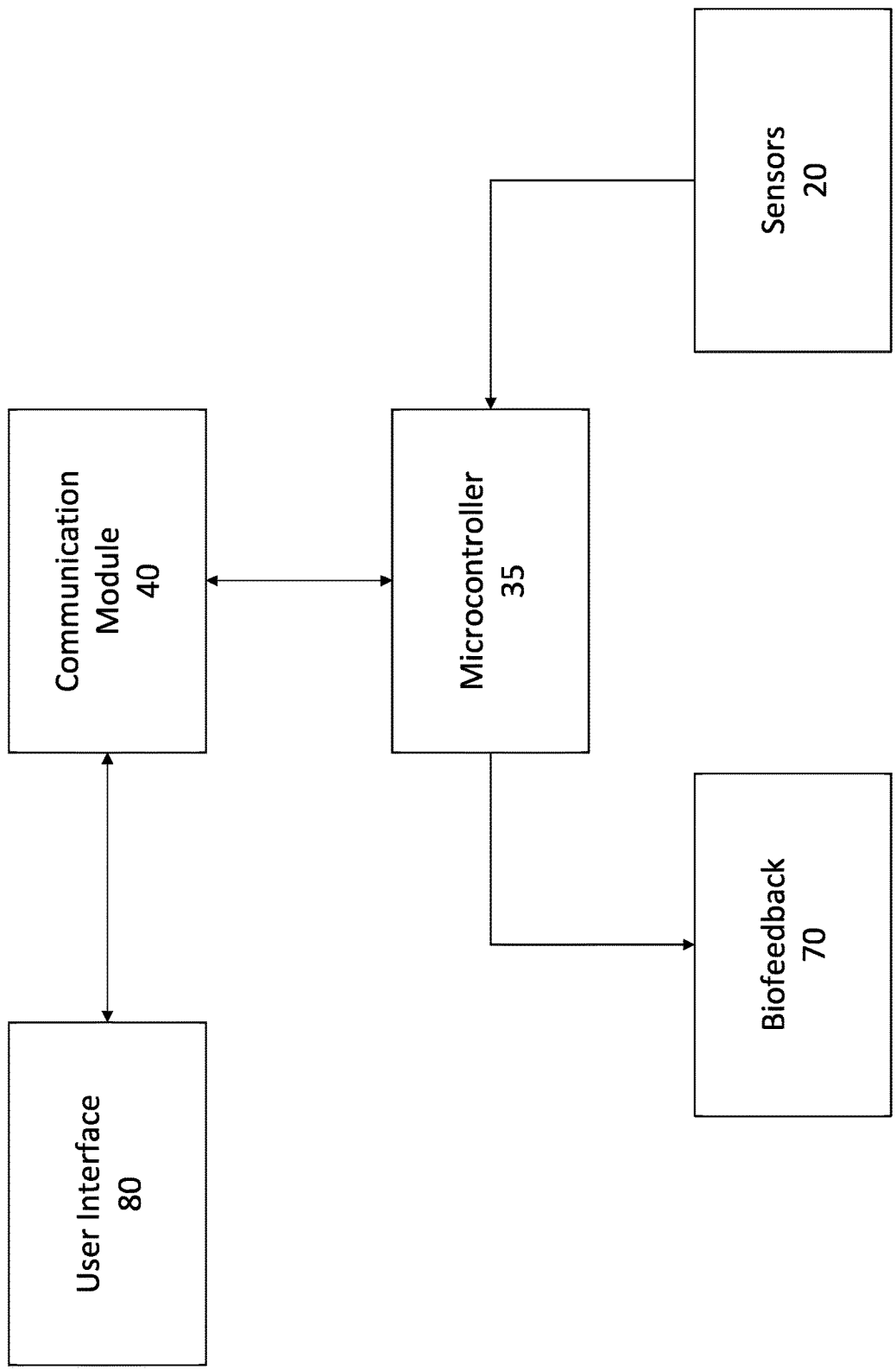
FIG. 7 is a schematic logic diagram of the interface, microcontroller, sensors, and biofeedback outputs.

FIG. 7 shows the communication of information throughout the insole system 10. The pressure sensors 20 provide information to the microcontroller 35 which controls the biofeedback 70. The microcontroller 35 passes information through the communication module 40 to the digital user interface 80. The microcontroller 35 will be contained within the control center 25 along with the communication module 40 and a rechargeable battery. In a preferred embodiment, an ESP32 is used as a microcontroller 35 and communication module 40. The control center 25 will contain a rechargeable battery within the insole that may be charged through inductive charging in a preferred embodiment. The preferred battery is a 1000 milliamp hour's lithium ion battery, which will last throughout the day so that the invention may be charged at night while the user is not wearing the insole.

Through communication of the device with a user interface 80 such as a computer application, a trained professional such as a doctor will be able to make adjustments to the device through the digital interface as needed by the user, allowing the invention to optimize its efficacy for each user. The Bluetooth will be used to control the pressure cuff 45 through a Bluetooth receiver located in an auxiliary control center 50 on the band 55 of the pressure cuff. The Bluetooth will also control the auditory device 65, which may be an existing Bluetooth headset that can be paired with the invention or may be designed separately in conjunction with this invention. Additionally, the invention may be paired with a hearing aid that has Bluetooth capabilities. The communication module 40 will also allow for communication with a computer through a digital user interface 80. Through communication of the device with a computer, a trained professional such as a doctor will be able to make adjustments to the device through the digital user interface as needed by the user, allowing the invention to optimize its efficacy for each user.

Operation

To operate the invention, the user must turn on a switch 60 which may be located on the headset, where it would be easily accessible to the user of the invention, or elsewhere on the system such as on the side of the insole 15. In a preferred embodiment, the switch will be a three-way switch, allowing the user to turn on the device and then choose between settings such as walking, driving, and charging. While walking, the user will use the switch to choose the setting designated for walking. In this setting, as the user puts their weight on each of the pressure sensors 20, the corresponding biofeedback stimuli 70 will be activated. These feedback stimuli include but are not limited to, vibration through the vibrating motors 30, pressure through the pressure cuff 45, and auditory stimulus 65 through a Bluetooth headset, or another comparable earpiece.

All feedback systems are activated in unison until the user shifts their weight onto the corresponding pressure sensors 20 and are deactivated as the user removes their weight from the corresponding pressure sensors 20. If the user puts pressure on their feet for an extended period of time, this will be detected by the pressure sensors 20 and microcontroller in the control center 25 and all forms of biofeedback 70 including vibration, pressure, and auditory stimulus will be deactivated until the user changes position again to prevent over-stimulation. It should be noted that other biofeedback stimuli 70 may be used, including visual stimulus through an LED which may be attached to the clothing of the user in any place that is visible to the wearer of the invention.

While driving, the user may use the switch to change the settings to driving mode. In this setting, the pressure sensors 20 will detect small changes in pressure, corresponding to changes in weight on the gas pedal. As the amount of pressure on the pedal changes, the biofeedback systems 70 will be activated with corresponding changes in magnitude. As pressure on the gas pedal increases, the magnitude of vibration in the vibrating motors 30 and pressure in the pressure cuff 45 will increase accordingly, as well as the pitch of the audio tone.

The invention 10 will be able to communicate with a computer via Bluetooth, allowing for easy adjustment of settings. The invention will include a user interface 80 to adjust all settings. The settings of the invention will be customizable to the needs of the user. Some of the settings that may be adjusted will include but are not limited to the response time of each of the biofeedback stimuli 70, as well as the sensitivity of the pressure sensors 20. The microcontroller 35 will store data on the gait of the user, such as the amount of steps taken and the time between each step. This data may be used by a doctor to analyze and monitor the gait of their patient. The interface may also provide visual feedback to the doctor, showing which parts of the foot are bearing the weight of the user by showing a map of the foot in the interface and changing the colors of different parts of the foot as the user shifts their weight on and off the pressure sensors 20.

Alternative Embodiment

It should be noted that the control center 25 is contained within the insole 10, but in alternate embodiments may be outside of the insole and can be attached to the shoe. The insole must be waterproof and durable to ensure that all electronic components are not damaged. It is recommended that the base of the insole be made of a hard, waterproof material, and that the control center 25 be contained in this part of the insole to prevent damage due to water or bending of the insole. On top of this hard base of the insole a foam or gel layer should form to the shape of the foot, as is common for most insoles, particularly those that are worn by people with peripheral neuropathy. This layer may be made of NickelPlast or another similar material. It should be noted that in FIGS. 1-5 the vibrating motors 30 and pressure sensors 20 are exposed to easily show the components of the device, however these components should be covered. In a preferred embodiment, the vibrating motors would be covered with a thin layer of waterproof foam or any other suitable comfortable material so that the motors are not in direct contact with the foot of the user and are not exposed to water damage, however the material should dampen the vibrations as little as possible so that it may be felt by the user. This foam layer may be customizable to the foot of the user like many custom made insoles, but may also be made in standard shoe sizes. The pressure sensors 20 on the bottom of the insole should be covered with a thin layer of a waterproof material that would protect from water damage but would not interfere with functionality of the pressure sensors by applying constant pressure to the pressure sensors. In a preferred embodiment a form of polyurethane would be used for this purpose. In order to prevent this layer from applying constant pressure to the sensors, adhesive should be placed around the pressure sensors but not on the pressure sensors before laying the plastic is laid on top of the adhesive, thereby fully encasing the pressure sensors between the plastic and the bottom of the insole.

The invention is not limited to the above description. Biofeedback systems may be altered to the needs of the user, so that it is possible to use some of the available feedback systems without using all of them. It should be noted that other feedback systems may be added to the device, including visual or electrical stimulation. Having described certain embodiments of the invention here, it should be noted that the invention is not limited to the above description or the attached exemplary drawings.

What is claimed is:

1. An insole system to improve gait stability comprising:
    at least one insert adapted to be inserted into a shoe to be worn by a user;
    sensors disposed inside said insert;
    a microcontroller attached to said insert, said microcontroller in communication with said sensors; and
    a plurality of output devices in communication with the microcontroller, adapted to be worn on the body of the user, said output devices providing feedback stimuli to the user correlating with user movement as detected by said sensors;
    wherein said output devices comprise a pressure cuff adapted to be worn on a limb of the user, wherein when at least one of said sensors is activated, said pressure cuff applies pressure to the limb upon which said pressure cuff is being worn.

2. An insole system according to claim 1, wherein said sensors are located at locations comprising at least two of i) beneath the ball of the foot, ii) beneath the heel of the foot, and iii) beneath the toe of the foot of the user when said insert is inserted into the shoe being worn by the user.

3. An insole system according to claim 1 further comprising a wireless communication system connecting said microcontroller to said output devices.

4. An insole system according to claim 3 further comprising a digital user interface that allows for modification of gait feedback parameters through said wireless communication system.

5. An insole system according to claim 4 wherein said user interface comprises a computer application in which functions of said sensors and said output devices are regulatable.

6. An insole system according to claim 4 wherein said user interface stores data recorded by said microcontroller and displays said data to the user.

7. An insole system according to claim 1 wherein said output devices comprise vibrating motors disposed on the insert and aligned with the sensors, wherein the strength of vibration of said motors correlates to the amount of pressure placed on said sensors.

8. An insole system according to claim 1 wherein said output devices comprise an audio device adapted to convey at least one audible tone to the user, wherein the audible tone correlates to the positions of said sensors.

9. An insole system according to claim 8, said output devices conveying a plurality of audible tones to the user, each of said plurality of audible tones respectively corresponding to one of said sensors, and wherein the volume of said plurality of audible tones correlates to the amount of pressure placed on the foot as sensed by said sensors.

10. An insole system according to claim 1 wherein said sensors comprise pressure sensors.

11. An insole system according to claim 1, further comprising a switch in communication with said microcontroller, said switch enabling the user to change settings of said insole from among a plurality of modes.

12. An insole system according to claim 11, wherein said plurality of modes comprises a walking mode for use when the user is walking and a driving mode for use when the user is driving.

13. An insole system to improve gait stability, comprising:
   at least one insert adapted to be inserted into a shoe to be worn by a user;
   sensors disposed inside said insert;
   a microcontroller attached to said insert, said microcontroller in communication with said sensors; and
   a plurality of output devices in communication with the microcontroller, adapted to be worn on the body of the user, said output devices providing feedback stimuli to the user correlating with user movement as detected by said sensors, said output devices comprising at least two of the following:
      i) vibrating motors disposed on said insert and aligned with the sensors, wherein the strength of vibration of said motors correlates to the amount of pressure placed on said sensors;
      ii) an audio device adapted to convey a plurality of different audible tones to the user, each of said plurality of different audible tones respectively corresponding to one of said sensors; and
      iii) a pressure cuff adapted to be worn on a limb of the user, wherein when at least one of said sensors is activated, said pressure cuff applies pressure to the limb upon which said pressure cuff is being worn.

14. An insole system according to claim 13, wherein said sensors are located at locations comprising at least two of i) beneath the ball of the foot, ii) beneath the heel of the foot, and iii) beneath the toe of the foot of the user when said insert is inserted into the shoe being worn by the user.

15. An insole system according to claim 13, wherein a volume of said plurality of different audible tones correlates to the amount of pressure placed on the foot as sensed by said sensors.

16. An insole system according to claim 13, further comprising a switch in communication with said microcontroller, said switch enabling the user to change settings of said insole from among a plurality of modes, wherein said plurality of modes includes a walking mode for use when the user is walking and a driving mode for use when the user is driving.

17. A method of improving gait stability, comprising the steps of:
   providing at least one insert adapted to be inserted into a shoe to be worn by a user, the insert having sensors disposed inside the insert and a microcontroller attached to the insole in communication with the sensors;
   providing a plurality of output devices in communication with the microcontroller, adapted to be worn on the body of the user, the output devices including at least two of the following:
      i) vibrating motors disposed on the insert and aligned with the sensors, wherein the strength of vibration of the motors correlates to the amount of pressure placed on the sensors;
      ii) an audio device adapted to convey a plurality of different audible tones to the user, each of the plurality of different audible tones respectively corresponding to one of the sensors; and
      iii) a pressure cuff adapted to be worn on a limb of the user, wherein when at least one of the sensors are activated, the pressure cuff applies pressure to the limb upon which the pressure cuff is being worn;
   detecting user movement via the sensors; and
   providing feedback stimuli to the user via the output devices correlating with user movement as detected by the sensors.

18. A method of improving gait stability according to claim 17, further comprising the steps of: providing a switch in communication with the microcontroller, and enabling the user to change settings of the insole from among a plurality of modes via the switch.

19. A method of improving gait stability according to claim 18, wherein the plurality of modes comprises a walking mode for use when the user is walking and a driving mode for use when the user is driving.

20. A method of improving gait stability according to claim 17, further comprising the step of locating the sensors at locations including at least two of i) beneath the ball of the foot, ii) beneath the heel of the foot, and iii) beneath the toe of the foot of the user when the insert is inserted into the shoe being worn by the user.

21. A method of improving gait stability according to claim 17, wherein a volume of the plurality of different audible tones correlates to the amount of pressure placed on the foot as sensed by the sensors.

* * * * *